United States Patent [19]

Ohsumi et al.

[11] Patent Number: 4,514,406
[45] Date of Patent: Apr. 30, 1985

[54] OXIME ETHERS AND THEIR USE

[75] Inventors: Tadashi Ohsumi, Funabashi; Makoto Hatakoshi, Minoo; Hirosi Kisida, Takarazuka, all of Japan

[73] Assignee: Sumitomo Chemical Company, Limited, Osaka, Japan

[21] Appl. No.: 466,905

[22] Filed: Feb. 16, 1983

[30] Foreign Application Priority Data

Mar. 4, 1982 [JP]   Japan .................................. 57-34553

[51] Int. Cl.³ ..................... A01N 43/40; A01N 33/24; C07C 131/00
[52] U.S. Cl. .................................... 514/352; 564/256; 546/264; 546/283; 546/284; 546/333; 546/334; 549/14; 549/30; 549/35; 549/59; 549/60; 549/74; 549/357; 549/414; 549/426; 549/430; 549/472; 549/491; 514/432; 514/436; 514/438; 514/442; 514/447; 514/452; 514/459; 514/467; 514/471; 514/472
[58] Field of Search ................ 564/256; 424/327, 263, 424/275, 276, 277, 278; 546/283, 284, 333, 334; 549/14, 30, 35, 59, 60, 74, 357, 430, 472, 491, 414, 426

[56] References Cited

U.S. PATENT DOCUMENTS 3,941,777 3/1976 Madsen et al. ..................... 564/256

FOREIGN PATENT DOCUMENTS 2806664 8/1978 Fed. Rep. of Germany ...... 424/327

Primary Examiner—Natalie Trousof
Assistant Examiner—Leah Hendriksen
Attorney, Agent, or Firm—Birch, Stewart, Kolasch & Birch

[57] ABSTRACT

A compound of the formula:

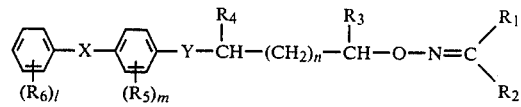

wherein $R_1$ and $R_2$ are, same or different, each a hydrogen atom, a $C_1$–$C_3$ alkyl group optionally substituted with halogen, an alkoxyalkyl or alkylthioalkyl group of the formula: $R_7$—Z—$(CH_2)_q$—, a $C_2$–$C_3$ alkenyl group, a $C_2$–$C_4$ alkynyl group, a $C_1$–$C_2$ alkoxy group, a $C_1$–$C_2$ alkylthio· group, a phenyl group, a pyridyl group, a furyl group or a thienyl group, or $R_1$ and $R_2$ may be combined together to form a saturated or unsaturated 5- or 6-membered ring having 0 to 2 oxygen or sulfur atom(s) within the ring, $R_3$ and $R_4$ are, same or different, each a hydrogen atom or a methyl group, $R_5$ is a methyl group or a halogen atom, $R_6$ is a $C_1$–$C_4$ alkyl group, a methoxy group, a halogen atom, a trifluoromethyl group or a nitro group, $R_7$ is a methyl group or an ethyl group, X is an oxygen atom, a sulfur atom or a methylene group, Y and Z are each an oxygen atom or a sulfur atom, l is an integer of 0 to 5, m is an integer of 0 to 4, n is an integer of 0 to 2 and q is an integer of 1 or 2, which is useful as an insect controlling agent.

24 Claims, No Drawings

OXIME ETHERS AND THEIR USE

The present invention relates to oxime ethers, and their production and use.

The said oxime ethers are representable by the formula:

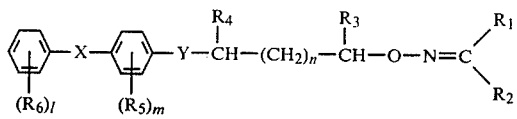

wherein $R_1$ and $R_2$ are, same or different, each a hydrogen atom, a $C_1$-$C_3$ alkyl group optionally substituted with halogen, an alkoxyalkyl or alkylthioalkyl group of the formula: $R_7$—$Z$—$(CH_2)_q$—, a $C_2$-$C_3$ alkenyl group, a $C_2$-$C_4$ alkynyl group, a $C_1$-$C_2$ alkoxy group, a $C_1$-$C_2$ alkylthio group, a phenyl group, a pyridyl group, a furyl group or a thienyl group, or $R_1$ and $R_2$ may be combined together to form a saturated or unsaturated 5- or 6-membered ring optionally having not more than 2 oxygen or sulfur atoms within the ring, $R_3$ and $R_4$ are, same or different, each a hydrogen atom or a methyl group, $R_5$ is a methyl group or a halogen atom, $R_6$ is a $C_1$-$C_4$ alkyl group, a methoxy group, a halogen atom, a trifluoromethyl group or a nitro group, $R_7$ is a methyl group or an ethyl group, X is an oxygen atom, a sulfur atom or a methylene group, Y and Z are each an oxygen atom or a sulfur atom, l is an integer of 0 to 5, m is an integer of 0 to 4, n is an integer of 0 to 2 and q is an integer of 1 or 2.

In the above significances, the term "halogen" includes chlorine, bromine, iodine or fluorine. Examples of the saturated or unsaturated 5- or 6-membered ring optionally having not more than 2 oxygen or suflur atoms within the ring are cyclopentane, cyclohexane, cyclohexene, tetrahydrofuran, tetrahydrothiophene, dithiolan, thian and benzocyclopentane, etc.

Among the oxime ethers (I), preferred are those wherein $R_1$ is a hydrogen atom or a methyl group, $R_2$ is a methyl group, an ethyl group or a vinyl group, $R_3$ and $R_4$ are, same or different, each a hydrogen atom or a methyl group, $R_6$ is a methyl group, a fluorine atom or a chlorine atom, X is an oxygen atom or a methylene group, Y is an oxygen atom, l is 0 or 1, m is 0 and n is 0.

The oxime ethers (I) can be prepared by various procedures, of which some typical examples are shown below.

Procedure A

A compound of the formula:

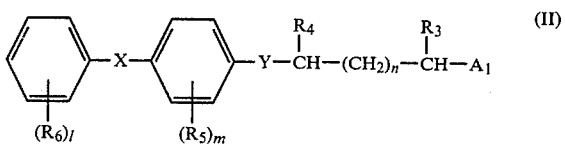

wherein $R_3$, $R_4$, $R_5$, $R_6$, X, Y, l, m and n are each as defined above and $A_1$ is a leaving group such as chlorine, bromine, iodine, mesyloxy or tosyloxy is reacted with a compound of the formula:

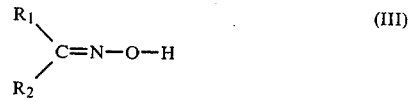

wherein $R_1$ and $R_2$ are each as defined above, or its alkali metal salt to give the ether oxime (I).

The reaction is usually carried out in an inert solvent (e.g. dimethylformamide, dimethylsulfoxide, tetrahydrofuran, dimethoxyethane, toluene) in the presence of an acid accepting agent such as an alkali metal (e.g. sodium, potassium), an alkali metal hydride, an alkali metal amide, an alkali metal hydroxide, an alkali metal carbonate (e.g. potassium carbonate) or an organic base at a temperature of $-30°$ C. to the boiling temperature of the solvent, preferably from room temperature to $100°$ C., for a period of 0.5 to 24 hours. In order to accelerate the reaction, a phase transfer catalyst such as benzyltriethylammonium chloride or tetra-n-butylammonium bromide may be employed. In this case, water may be used as the solvent.

The molar ratio of the compound (II) and the compound (III) is usually 1:1-3, preferably 1:1.1-1.2.

Procedure B

A compound of the formula:

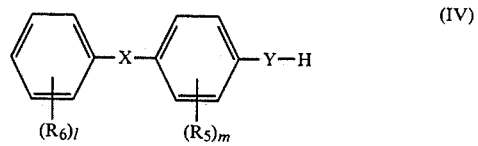

wherein $R_5$, $R_6$, X, Y, l and m are each as defined above, or its alkali metal salt is reacted with a compound of the formula:

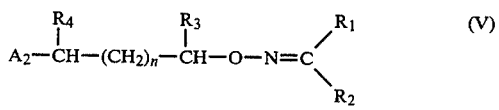

wherein $R_1$, $R_2$, $R_3$, $R_4$ and n are each as defined above and $A_2$ is a leaving group such as chlorine, bromine, iodine, mesyloxy or tosyloxy to give the oxime ether (I).

The reaction is normally carried out in an inert solvent (e.g. dimethylformamide, dimethylsulfoxide, tetrahydrofuran, dimethoxyethane, toluene) in the presence of an acid accepting agent such as an alkali metal (e.g. sodium, potassium), an alkali metal hydride, an alkali metal amide, an alkali metal hydroxide, an alkali metal carbonate (e.g. potassium carbonate) or an organic base at a temperature of $-30°$ C. to the boiling temperature of the solvent, favorably from room temperature to $100°$ C., for a period of 0.5 to 24 hours. In order to accelerate the reaction, a phase transfer catalyst such as benzyltriethylammonium chloride or tetra-n-butylammonium bromide is usable. In such case, water may be employed as the solvent.

The molar ratio of the compound (IV) and the compound (V) is usually 1:0.33-3, preferably 1:0.8-1.2.

Procedure C

A compound of the formula:

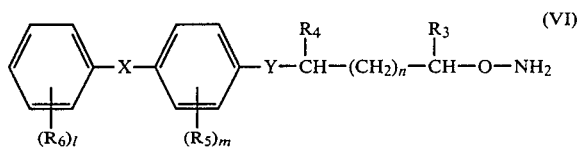

wherein $R_3$, $R_4$, $R_5$, $R_6$, X, Y, l, m and n are each as defined above, or its reactive derivative is reacted with a compound of the formula:

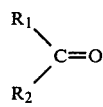

wherein $R_1$ and $R_2$ are each as defined above, or its reactive derivative to give the oxime ether (I).

As the reactive derivative of the compound (VI), there may be exemplified the mineral acid salts (e.g. hydrochloride, sulfate), the organic acid salts, the oxime ethers, etc. Any derivative of the compound (VI) which can afford the compound (VI) itself under the condition of the reaction system falls within the category of the "reactive derivative". Examples of the reactive derivative (VII) include the acetals, the ketals, the hemiacetals, the hemiketals, the hydrates, etc. Any derivative of the compound (VII) which can afford the compound (VII) itself under the condition of the reaction system may be understood to fall within the category of the "reactive derivative".

The reaction may be carried out in the presence or absence of an inert solvent (e.g. water, benzene, toluene, carbon tetrachloride, chloroform, ethylene chloride, methylene chloride) and/or an acid (e.g. hydrochloric acid, sulfuric acid, p-toluenesulfonic acid) or a base (e.g. sodium hydroxide, potassium hydroxide, potassium carbonate, triethylamine, pyridine), usually at a temperature of $-30°$ C. to the boiling temperature of the solvent, preferably from room temperature to 100° C., for a period of 0.5 to 24 hours.

The molar ratio of the compound (IV) and the compound (VII) is normally 1:1–20, preferably 1:1.1–1.2.

In the above procedures, the recovery of the produced oxime ether (I) from the reaction mixture and the purification of the recovered oxime ether (I) may be carried out by per se conventional procedures. For instance, the purification can be achieved by chromatography, distillation, etc.

The oxime ether (I) has optical isomers with respect to the groups $R_3$ and $R_4$ and geometrical isomers with respect to the groups $R_1$ and $R_2$, and all of them are included within the scope of the invention.

The compound (II) as one of the starting materials may be produced by per se conventional procedures, of which typical examples are shown in the following formulas:

Route I:

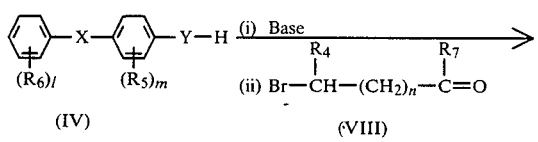

-continued
Route I:

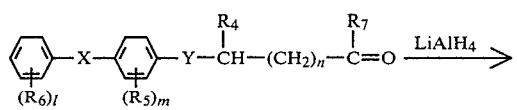

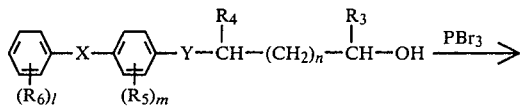

(II: $A_1$ = Br)

wherein $R_3$, $R_4$, $R_5$, $R_6$, X, Y, l, m and n are each as defined above, $R_7$ is a group of the formula: $-OR_8$ (wherein $R_8$ is a $C_1$–$C_3$ alkyl group) in case of $R_3$ being a hydrogen atom or $R_7$ is a methyl group in case of $R_3$ being a methyl group.

Route II:

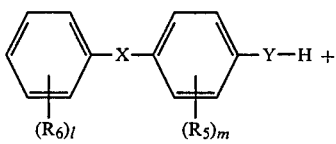

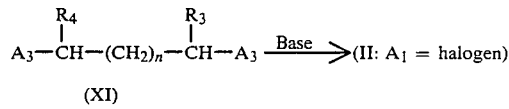

wherein $R_3$, $R_4$, $R_5$, $R_6$, X, Y, l, m and n are each as defined above and $A_3$ is a halogen atom.

The compound (III) is known or can be prepared by per se conventional procedures (cf. Org.Synth., Coll. Vol. II, 313 (1943).

The compound (IV) is known or can be prepared by per se conventional procedures (cf. Angew.Chem., 52, 915 (1938); Japanese Patent Publn. (unexamined) No. 62033/1980).

The compound (V) may be prepared by per se conventional procedures, of which typical examples are as follows:

Route I:

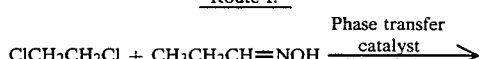

$ClCH_2CH_2O-N=CHCH_2CH_3$
(V: $R_1$ = H; $R_2$ = $C_2H_5$;
$R_3$ = H; $R_4$ = H; $A_2$ = Cl;
n = 0)

Route II:

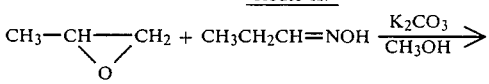

-continued

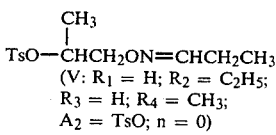

(V: $R_1$ = H; $R_2$ = $C_2H_5$; $R_3$ = H; $R_4$ = $CH_3$; $A_2$ = TsO; n = 0)

The compound (VI) can be prepared by per se conventional procedures (cf. J.Org.Chem., 28, 1604 (1963); Japanese Patent Publns. (unexamined) Nos. 144571/1978 and 147014/1978), of which a typical example is shown below:

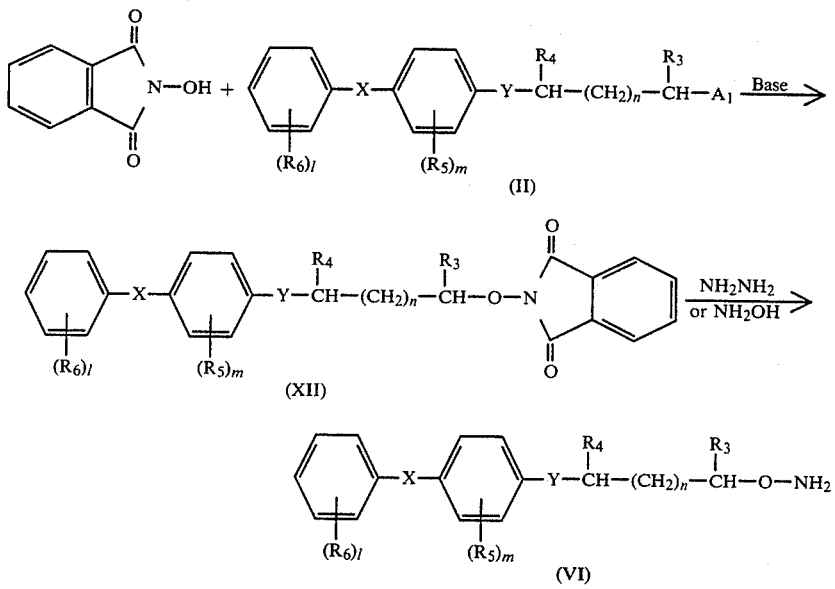

wherein $R_3$, $R_4$, $R_5$, $R_6$, X, Y, $A_1$, l, m and n are each as defined above.

Some practical embodiments of the procedures for preparation of the oxime ether (I) are shown in the following Examples.

EXAMPLE 1

(Production of Compound No. 2 according to Procedure A)

Propionaldoxime (0.73 g; 10.0 mmol) was dissolved in dimethylformamide (10 ml), and the resulting mixture was stirred at an inner temperature of 10° C. under ice-cooling, followed by addition of sodium hydride (0.24 g; 10.0 mmol). After completion of the reaction, stirring was continued for 2 hours, and a solution of 2-(4-phenoxyphenoxy)ethyl tosylate (3.20 g; 8.33 mmol) in dimethylformamide (10 ml) was dropwise added thereto. The resultant mixture was stirred at room temperature overnight, poured into water and extracted with ethyl acetate. The extract was washed with water and concentrated. The residue was purified by silica gel column chromatography using benzene as an eluent to give 1.50 g of Compound No. 2 as a pale yellow oily substance in a yield of 52.6%. $n_D^{25.0}$=1.5577.

EXAMPLE 2

(Production of Compound No. 24 according to Procedure A)

2-Hydroxyiminotetrahydrothiophene (0.50 g; 4.27 mmol) was dissolved in dimethylformamide (10 ml), and the resulting mixture was stirred at an inner temperature of 10° C. under ice-cooling, followed by addition of sodium hydride (0.10 g; 4.27 mmol). After completion of the reaction, stirring was continued for 2 hours, and a solution of 1-bromo-2-(4-phenoxyphenoxy)ethane (1.04 g; 3.56 mmol) in dimethylformamide (5 ml) was dropwise added thereto. The resultant mixture was stirred at room temperature overnight, poured into water and extracted with ethyl acetate. The extract was washed with water and concentrated. The precipitated crystals were collected, washed with n-hexane and dried to give 0.80 g of Compound No. 24 in a yield of 52.6%. M.P., 107.6° C.

EXAMPLE 3

(Production of Compound No. 97 according to Procedure B)

4-Phenoxyphenol (1.86 g; 10.0 mmol) was dissolved in dimethylformamide (10 ml), and the resulting mixture was stirred at an inner temperature of 10° C. under ice-cooling, followed by addition of sodium hydride (0.24 g; 10.0 mmol). After completion of the reaction, stirring was continued for 2 hours, and a solution of O-{3-(p-toluenesulfonyloxy)propyl}propionaldoxime (2.28 g; 8.0 mmol) in dimethylformamide (10 ml) was dropwise added thereto. The resultant mixture was stirred at 80°-100° C. overnight, poured into water and extracted with ethyl acetate. The extract was washed with water and concentrated. The residue was purified by silica gel column chromatography using benzene as an eluent to give 1.20 g of Compound No. 97 as a pale yellow oily substance in a yield of 40.1%. $n_D^{23.0}$=1.5584.

EXAMPLE 4

(Production of Compound No. 9 according to Procedure C)

To a solution of O-{2-(4-phenoxyphenoxy)ethyl}-hydroxylamine (0.25 g; 10.0 mmol) in chloroform (5 ml), there was dropwise added a 30% aqueous solution of chloroacetaldehyde (0.52 g) in 10 minutes, followed by stirring at room temperature overnight. The reaction mixture was poured into water, dried over anhydrous sodium sulfate and concentrated, whereby there was obtained an oily substance, which was then purified by silica gel column chromatography using methylene chloride as an eluent to give 0.24 g of Compound No. 9 as a transparent oily substance in a yield of 78.5%. $n_D^{22.5} = 1.5712$.

EXAMPLE 5

(Production of Compound No. 2 according to Procedure C)

Compound No. 5 (prepared in the same manner as in Example 1 but using acetoxime in place of propionaldoxime) (0.05 g; 0.18 mmol) and propionaldehyde (0.02 g; 3.5 mmol) were dissolved in methanol (1 g) and, after addition of one drop of conc. sulfuric acid, the resultant mixture was refluxed for 3 hours to complete the reaction. The reaction mixture was cooled to room temperature and water (20 ml) was added thereto, followed by extraction with chloroform (10 ml) twice. The extract was dried over anhydrous sodium sulfate and concentrated to give an oily product. By a gas chromatographic analysis, this product was determined to contain 88% of Compound No. 2.

In the same manner as above, there were prepared the oxime ethers (I), of which some examples are shown in Table 1.

TABLE 1

| Compound No. | X | Y | $R_1$ | $R_2$ | $R_3$ | $R_4$ | $(R_5)_m$ | $(R_6)_l$ | n | Physical constant |
|---|---|---|---|---|---|---|---|---|---|---|
| 1 | O | O | H | CH$_3$ | H | H | H | H | 0 | $n_D^{24.0}$ 1.5598 |
| 2 | O | O | H | C$_2$H$_5$ | H | H | H | H | 0 | $n_D^{25.0}$ 1.5577 |
| 3 | O | O | H | n-C$_3$H$_7$ | H | H | H | H | 0 | $n_D^{23.5}$ 1.5505 |
| 4 | O | O | H | i-C$_3$H$_7$ | H | H | H | H | 0 | $n_D^{21.5}$ 1.5548 |
| 5 | O | O | CH$_3$ | CH$_3$ | H | H | H | H | 0 | M.P. 60–61° C. |
| 6 | O | O | CH$_3$ | C$_2$H$_5$ | H | H | H | H | 0 | $n_D^{25.5}$ 1.5498 |
| 7 | O | O | C$_2$H$_5$ | C$_2$H$_5$ | H | H | H | H | 0 | $n_D^{23.0}$ 1.5460 |
| 8 | O | O | H | CF$_3$ | H | H | H | H | 0 | $n_D^{23.5}$ 1.5270 |
| 9 | O | O | H | CH$_2$Cl | H | H | H | H | 0 | $n_D^{22.5}$ 1.5712 |
| 10 | O | O | H | CCl$_3$ | H | H | H | H | 0 | $n_D^{22.0}$ 1.5720 |
| 11 | O | O | H | —CH=CH$_2$ | H | H | H | H | 0 | $n_D^{24.0}$ 1.5752 |
| 12 | O | O | H | —CH=CHCH$_3$ | H | H | H | H | 0 | $n_D^{23.0}$ 1.5757 |
| 13 | O | O | CH$_3$ | —CH$_2$OCH$_3$ | H | H | H | H | 0 | $n_D^{20.5}$ 1.5512 |
| 14 | O | O | CH$_3$ | SCH$_3$ | H | H | H | H | 0 | $n_D^{25.0}$ 1.5870 |
| 15 | O | O | CH$_3$ |  | H | H | H | H | 0 | M.P. 73.9° C. |
| 16 | O | O | H | 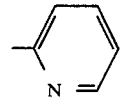 | H | H | H | H | 0 | M.P. 80.7° C. |
| 17 | O | O | H | 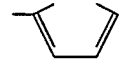 | H | H | H | H | 0 | M.P. 74–76° C. |
| 18 | O | O | H | 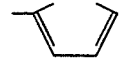 | H | H | H | H | 0 | $n_D^{24.0}$ 1.5942 |
| 19 | O | O | H | 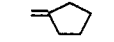 | H | H | H | H | 0 | $n_D^{23.0}$ 1.6023 |
| 20 | O | O | 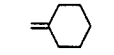 | | H | H | H | H | 0 | M.P. 72.6° C. |
| 21 | O | O | 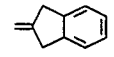 | | H | H | H | H | 0 | $n_D^{24.0}$ 1.5667 |
| 22 | O | O | 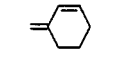 | | H | H | H | H | 0 | M.P. 50–55° C. |
| 23 | O | O | 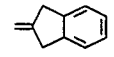 | | H | H | H | H | 0 | $n_D^{24.0}$ 1.5859 |

TABLE 1-continued

Structure:

phenyl-$(R_6)_l$—X—phenyl-$(R_5)_m$—Y—CH($R_4$)—(CH$_2$)$_n$—CH($R_3$)—O—N=C($R_1$)($R_2$)

| Compound No. | X | Y | R$_1$ | R$_2$ | R$_3$ | R$_4$ | (R$_5$)$_m$ | (R$_6$)$_l$ | n | Physical constant |
|---|---|---|---|---|---|---|---|---|---|---|
| 24 | O | O | =S-cyclopentane | | H | H | H | H | 0 | M.P. 107.6° C. |
| 25 | O | O | =S,S-dithiolane | | H | H | H | H | 0 | M.P. 107.2° C. |
| 26 | O | O | =S-cyclohexane | | H | H | H | H | 0 | M.P. 79.3° C. |
| 27 | O | O | =O-tetrahydrofuran | | H | H | H | H | 0 | $N_D^{22.0}$ 1.5708 |
| 1 | O | O | H | CH$_3$ | H | H | H | H | 0 | $n_D^{27.5}$ 1.5494 |
| 29 | O | O | H | C$_2$H$_5$ | H | CH$_3$ | H | H | 0 | $n_D^{22.5}$ 1.5473 |
| 30 | O | O | H | C$_2$H$_5$ | H | H | 2-CH$_3$ | H | 0 | $n_D^{21.5}$ 1.5534 |
| 31 | O | O | H | C$_2$H$_5$ | H | H | 3-CH$_3$ | H | 0 | $n_D^{21.5}$ 1.5481 |
| 32 | O | O | H | CH$_3$ | H | H | H | 2-CH$_3$ | 0 | $n_D^{25.0}$ 1.5558 |
| 33 | O | O | H | CH$_3$ | H | H | H | 3-CH$_3$ | 0 | $n_D^{26.0}$ 1.5561 |
| 34 | O | O | H | CH$_3$ | H | H | H | 4-CH$_3$ | 0 | $n_D^{27.0}$ 1.5572 |
| 35 | O | O | CH$_3$ | CH$_3$ | H | H | H | 2-CH$_3$ | 0 | M.P. 63–66° C. |
| 36 | O | O | CH$_3$ | CH$_3$ | H | H | H | 3-CH$_3$ | 0 | $n_D^{25.0}$ 1.5508 |
| 37 | O | O | CH$_3$ | CH$_3$ | H | H | H | 4-CH$_3$ | 0 | $n_D^{25.0}$ 1.5538 |
| 38 | O | O | H | C$_2$H$_5$ | H | H | H | 2-CH$_3$ | 0 | $n_D^{23.0}$ 1.5486 |
| 39 | O | O | H | C$_2$H$_5$ | H | H | H | 3-CH$_3$ | 0 | $n_D^{24.0}$ 1.5530 |
| 40 | O | O | H | C$_2$H$_5$ | H | H | H | 4-CH$_3$ | 0 | $n_D^{22.5}$ 1.5522 |
| 41 | O | O | H | CH$_3$ | H | H | H | 3-C$_2$H$_5$ | 0 | $n_D^{24.0}$ 1.5542 |
| 42 | O | O | H | C$_2$H$_5$ | H | H | H | 3-C$_2$H$_5$ | 0 | $n_D^{24.0}$ 1.5488 |
| 43 | O | O | H | CH$_3$ | H | H | H | 3-i-C$_3$H$_7$ | 0 | $n_D^{23.0}$ 1.5509 |
| 44 | O | O | H | C$_2$H$_5$ | H | H | H | 3-i-C$_3$H$_7$ | 0 | $n_D^{23.0}$ 1.5463 |
| 45 | O | O | H | CH$_3$ | H | H | H | 3-t-C$_4$H$_9$ | 0 | $n_D^{24.0}$ 1.5478 |
| 46 | O | O | H | C$_2$H$_5$ | H | H | H | 3-t-C$_4$H$_9$ | 0 | $n_D^{23.0}$ 1.5440 |
| 47 | O | O | H | CH$_3$ | H | H | H | 2-F | 0 | M.P. 47–50° C. |
| 48 | O | O | H | CH$_3$ | H | H | H | 3-F | 0 | $n_D^{24.0}$ 1.5472 |
| 49 | O | O | H | CH$_3$ | H | H | H | 4-F | 0 | $n_D^{23.0}$ 1.5478 |
| 50 | O | O | CH$_3$ | CH$_3$ | H | H | H | 2-F | 0 | — |
| 51 | O | O | CH$_3$ | CH$_3$ | H | H | H | 3-F | 0 | $n_D^{24.0}$ 1.5432 |
| 52 | O | O | CH$_3$ | CH$_3$ | H | H | H | 4-F | 0 | $n_D^{22.0}$ 1.5440 |
| 53 | O | O | H | C$_2$H$_5$ | H | H | H | 2-F | 0 | $n_D^{24.0}$ 1.5437 |
| 54 | O | O | H | C$_2$H$_5$ | H | H | H | 3-F | 0 | $n_D^{24.0}$ 1.5422 |
| 55 | O | O | H | C$_2$H$_5$ | H | H | H | 4-F | 0 | $n_D^{24.0}$ 1.5430 |
| 56 | O | O | H | CH$_3$ | H | H | H | 2-Cl | 0 | $n_D^{24.0}$ 1.5198 |
| 57 | O | O | H | CH$_3$ | H | H | H | 3-Cl | 0 | $n_D^{24.0}$ 1.5807 |
| 58 | O | O | H | CH$_3$ | H | H | H | 4-Cl | 0 | $n_D^{30.0}$ 1.5668 |
| 59 | O | O | CH$_3$ | CH$_3$ | H | H | H | 2-Cl | 0 | — |
| 60 | O | O | CH$_3$ | CH$_3$ | H | H | H | 3-Cl | 0 | $n_D^{24.0}$ 1.5623 |
| 61 | O | O | CH$_3$ | CH$_3$ | H | H | H | 4-Cl | 0 | M.P. 44–48° C. |
| 62 | O | O | H | C$_2$H$_5$ | H | H | H | 2-Cl | 0 | — |
| 63 | O | O | H | C$_2$H$_5$ | H | H | H | 3-Cl | 0 | $n_D^{24.0}$ 1.5681 |
| 64 | O | O | H | C$_2$H$_5$ | H | H | H | 4-Cl | 0 | $n_D^{23.0}$ 1.5630 |
| 65 | O | O | H | CH$_3$ | H | H | H | 2-Br | 0 | M.P. 61–63° C. |
| 66 | O | O | H | CH$_3$ | H | H | H | 3-Br | 0 | $n_D^{24.0}$ 1.5813 |
| 67 | O | O | H | CH$_3$ | H | H | H | 2-Br | 0 | — |
| 68 | O | O | CH$_3$ | CH$_3$ | H | H | H | 3-Br | 0 | $n_D^{24.0}$ 1.5756 |
| 69 | O | O | H | C$_2$H$_5$ | H | H | H | 2-Br | 0 | $n_D^{24.0}$ 1.5709 |
| 70 | O | O | H | C$_2$H$_5$ | H | H | H | 3-Br | 0 | $n_D^{24.0}$ 1.5747 |
| 71 | O | O | H | CH$_3$ | H | H | H | 2-CF$_3$ | 0 | $n_D^{24.0}$ 1.5217 |
| 72 | O | O | H | CH$_3$ | H | H | H | 3-CF$_3$ | 0 | $n_D^{24.0}$ 1.5230 |
| 73 | O | O | H | CH$_3$ | H | H | H | 4-CF$_3$ | 0 | M.P. 44–50° C. |
| 74 | O | O | CH$_3$ | CH$_3$ | H | H | H | 2-CF$_3$ | 0 | — |

TABLE 1-continued

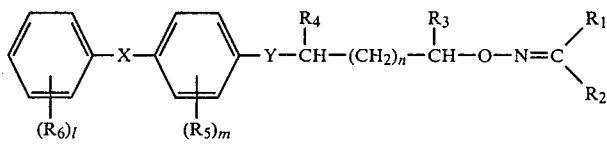

| Compound No. | X | Y | R1 | R2 | R3 | R4 | (R5)m | (R6)l | n | Physical constant |
|---|---|---|---|---|---|---|---|---|---|---|
| 75 | O | O | CH3 | CH3 | H | H | H | 3-CF3 | 0 | $n_D^{24.0}$ 1.5185 |
| 76 | O | O | CH3 | CH3 | H | H | H | 4-CF3 | 0 | $n_D^{24.0}$ 1.5177 |
| 77 | O | O | H | C2H5 | H | H | H | 2-CF3 | 0 | $n_D^{24.0}$ 1.5182 |
| 78 | O | O | H | C2H5 | H | H | H | 3-CF3 | 0 | $n_D^{24.0}$ 1.5148 |
| 79 | O | O | H | C2H5 | H | H | H | 4-CF3 | 0 | $n_D^{23.0}$ 1.5603 |
| 80 | O | O | H | C2H5 | H | H | H | 3-NO2 | 0 | $n_D^{24.0}$ 1.5752 |
| 81 | O | O | H | CH3 | H | H | H | 3-OCH3 | 0 | $n_D^{24.0}$ 1.5621 |
| 82 | O | O | H | CH3 | H | H | H | 4-OCH3 | 0 | — |
| 83 | O | O | CH3 | CH3 | H | H | H | 3-OCH3 | 0 | — |
| 84 | O | O | CH3 | CH3 | H | H | H | 4-OCH3 | 0 | $n_D^{23.0}$ 1.5577 |
| 85 | O | O | H | C2H5 | H | H | H | 3-OCH3 | 0 | $n_D^{24.0}$ 1.5559 |
| 86 | O | O | H | C2H5 | H | H | H | 4-OCH3 | 0 | M.P. 55–59° C. |
| 87 | S | O | H | C2H5 | H | H | H | H | 0 | $n_D^{23.0}$ 1.6018 |
| 88 | CH2 | O | H | CH3 | H | H | H | H | 0 | $n_D^{27.0}$ 1.5618 |
| 89 | CH2 | O | CH3 | CH3 | H | H | H | H | 0 | M.P. 40–42° C. |
| 90 | CH2 | O | H | C2H5 | H | H | H | H | 0 | $n_D^{22.5}$ 1.5584 |
| 91 | CH2 | O | H | C2H5 | H | H | H | 2-F | 0 | $n_D^{25.0}$ 1.5452 |
| 92 | CH2 | O | H | C2H5 | H | H | H | 3-F | 0 | $n_D^{25.0}$ 1.5437 |
| 93 | CH2 | O | H | C2H5 | H | H | H | 4-F | 0 | $n_D^{25.0}$ 1.5445 |
| 94 | CH2 | O | H | C2H5 | H | H | H | 4-OCH3 | 0 | M.P. 61.5° C. |
| 95 | CH2 | O | H | C2H5 | H | CH3 | H | H | 0 | $n_D^{24.0}$ 1.5492 |
| 96 | O | S | H | C2H5 | H | H | H | H | 0 | $n_D^{24.0}$ 1.5857 |
| 97 | O | O | H | C2H5 | H | H | H | H | 1 | $n_D^{23.0}$ 1.5584 |
| 98 | O | O | H | C2H5 | CH3 | H | H | H | 1 | $n_D^{22.0}$ 1.5413 |
| 99 | O | S | H | C2H5 | H | H | H | H | 1 | $n_D^{22.5}$ 1.5767 |
| 100 | O | O | H | C2H5 | H | H | H | H | 2 | $n_D^{23.5}$ 1.5552 |

101

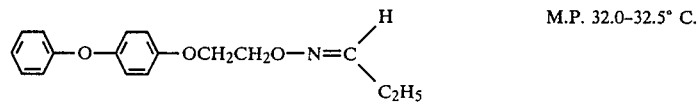

(Syn-isomer of Compound No. 2)

M.P. 32.0–32.5° C.

102

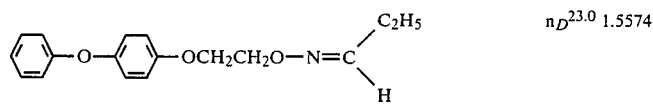

(Anti-isomer of Compound No. 2)

$n_D^{23.0}$ 1.5574

103

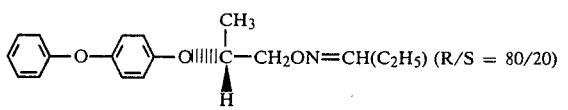

((R)-isomer of Compound No. 29)

$[\alpha]_D$ −22.4° (CHCl3, 0.41)

104

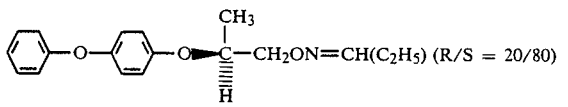

((S)-isomer of Compound No. 29)

$[\alpha]_D$ +18.1° (CHCl3, 0.27)

| 105 | O | O | H | CH3 | H | H | H | 3,5-Cl2 | 0 | $n_D^{24.0}$ 1.5781 |
|---|---|---|---|---|---|---|---|---|---|---|
| 106 | O | O | H | C2H5 | H | H | H | 3,5-Cl2 | 0 | $n_D^{24.0}$ 1.5718 |
| 107 | O | O | H | CH3 | H | CH3 | H | 3,5-Cl2 | 0 | — |
| 108 | O | O | H | C2H5 | H | CH3 | H | 3,5-Cl2 | 0 | $n_D^{25.0}$ 1.5605 |
| 109 | O | O | H | C2H5 | H | H | H | 3,5-(CH3)2 | 0 | $n_D^{25.0}$ 1.5507 |
| 110 | O | O | H | C2H5 | H | CH3 | H | 3,5-(CH3)2 | 0 | — |
| 111 | O | O | H | CH3 | H | H | H | 3,5-F2 | 0 | $n_D^{25.0}$ 1.5421 |
| 112 | O | O | H | C2H5 | H | H | H | 3,5-F2 | 0 | $n_D^{25.0}$ 1.5364 |
| 113 | O | O | H | CH3 | H | CH3 | H | 3,5-F2 | 0 | — |
| 114 | O | O | H | C2H5 | H | CH3 | H | 3,5-F2 | 0 | $n_D^{25.0}$ 1.5251 |
| 115 | O | O | H | CH3 | H | CH3 | H | 3-F | 0 | $n_D^{24.0}$ 1.5399 |
| 116 | O | O | H | C2H5 | H | CH3 | H | 3-F | 0 | $n_D^{24.0}$ 1.5348 |
| 117 | O | O | H | CH3 | H | H | H | H | 1 | $n_D^{22.5}$ 1.5545 |

TABLE 1-continued

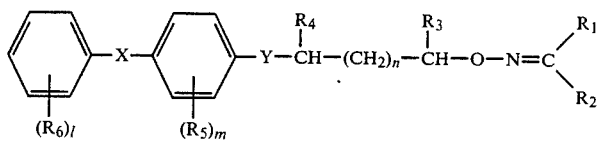

| Compound No. | X | Y | $R_1$ | $R_2$ | $R_3$ | $R_4$ | $(R_5)_m$ | $(R_6)_l$ | n | Physical constant |
|---|---|---|---|---|---|---|---|---|---|---|
| 118 | O | O | H | H | H | H | H | H | 2 | M.P. 57.4° C. |
| 119 | O | O | H | H | H | H | H | H | 0 | M.P. 67.3° C. |
| 120 | $CH_2$ | O | H | $CH_3$ | H | $CH_3$ | H | H | 0 | $n_D^{24.0}$ 1.5531 |
| 121 | O | O | $CH_3$ | $OCH_3$ | H | H | H | H | 0 | $n_D^{25.0}$ 1.5795 |
| 122 | O | O | H | $-C\equiv CH$ | H | H | H | H | 0 | $n_D^{25.0}$ 1.5706 |

It has been hitherto known that the organic phosphorus series insecticides, organic chlorine series insecticides or carbamate series insecticides largely contribute to the prevention of harmful insects. Some of these insecticides, however, exhibit a high phytotoxicity so that their residual effect has posed a serious problem on the abnormal ecosystem of the insects. Further, a resistivity to the insecticides has recently become noticed in certain insects such as house flies, planthoppers, leafhoppers, rice borers, etc.

In order to solve the drawbacks as seen in the conventional insecticides, an extensive study was carried out to provide an excellent insecticide which shows at a low concentration a high preventive effect attributable to a juvenile hormone-like controlling activity. As a result, it has now been found that the oxime ether (I) of the invention are useful for the control of insects in agricultural fields, forest lands, granaries, stored products and sanitary facilities, etc.

As the insecticide having a juvenile hormone-like controlling activity, "methoprene" is available (U.S. Pat. Nos. 3,904,662 and 3,912,815). This known insecticide is still not satisfactory.

The oxime ethers (I) of the invention show a juvenile hormone-like controlling effect and therefore can be used in low concentration for the control of a variety of insects belonging to Hemiptera, Lepidoptera, Coleoptera, Diptera, Dictyoptera, Orthoptera, Homoptera, Hymenoptera and Aphaniptera in agricultural fields, forest lands, granaries, stored products and sanitary facilities, etc., of which specific examples are as follows:

1. Hemiptera:
smaller brown planthopper (*Laodelphax striatellus*), brown planthopper (*Nilaparvata lugens*), whitebacked planthopper (*Sogatella furcifera*), green rice leafhopper (*Nephotettix cincticeps*), rice stink bug (*Lagynotomus elongatus*), common green stink bug (*Nezara antennata*), white-spotted bug (*Eysarcaris ventralis*), green peach aphid (*Myzus persicae*), cotton aphid (*Aphis gossypii*), cabbage aphid (*Brevicoryne brassicae*), cottony cushion scale (*Icerya purchasi*), citrus mealy bug (*Planococcus citri*), arrowhead scale (*Unaspis yanonensis*), etc.

2. Lepidoptera:
tobacco cutworm (*Spodoptera litura*), rice stem borer (*Chilo suppressalis*), grass leaf roller (*Cnaphalocrocis medinalis*), wax moth (*Galleria mellonella*), diamond back moth (*Pluttella xylostella*), smaller tea tortrix (*Adoxophyes* sp.), common white (*Pieris rapae*), cabbage armyworm (*Mamestra brassicae*), armyworm (*Pseudaletia separate*), etc.

3. Coleoptera:
varied carpet beetle (*Anthrenus verbasci*), lyctus powder-post beetle (*Lyctus brunneus*), rice leaf beetle (*Onlema oryzae*), rice plant weevil (*Echinocnemus squameus*), 28-spotted lady beetle (*Henosepilachna vigintioctopunctata*), cupreous beetle (*Anomala cuprea*), japanese beetle (*Popilla japonica*), tobacco beetle (*Lasioderma serricorne*), etc.

4. Diptera:
housefly (*Musca domestica*), melon fly (*Dacus cucurbitae*), common mosquito (*Culex pipiens pallens*), yellow fever mosquito (*Aedes aegypti*), malaria mosquito (*Anopheles* sp.), etc.

5. Dictyoptera:
German cockroach (*Blattella germanica*), smoky brown cockroach (*Periplaneta fuliginosa*), etc.

In a practical application as insect control agents, the oxime ethers (I) are used in the form of an appropriate composition such as emulsifiable concentrates, dusts, granules, wettable powders, fine granules and aerosols and the content of the oxime ether (I) in such composition may be from about 0.1 to 99.9% by weight, preferably from about 2.0 to 80.0% by weight.

The composition can be formulated in a per se conventional manner by mixing at least one of the oxime ethers (I) with an appropriate solid or liquid carrier(s) or diluent(s) with or without an appropriate adjuvant(s) (e.g. surfactants, adherents, dispersants, stabilizers) for improving the dispersibility and other properties of the active ingredient on use.

Examples of the solid carriers or diluents are clays (e.g. kaolin, bentonite, fuller's earth, pyrophyllite, sericite), talcs, other inorganic materials (e.g. hydrated silica, pumice, diatomaceous earth, sulfur powder, active carbon) in fine powders or powdery form.

Examples of the liquid carriers or diluents are alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride), etc.

Examples of the surfactants are alkylsulfates, alkylsulfonates, alkylarylsulfonates, polyethylene glycol ethers, polyhydric alcohol esters, etc. Examples of the adherents and dispersants may include casein, gelatin, starch powder, carboxymethyl cellulose, gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

In addition, the said composition may contain insecticides, insect growth inhibitors, acaricides, nematocides, fungicides, herbicides, plant growth regulators, fertilizers, soil improvers, etc. Particularly when employed in conjunction with conventional insecticides, a broad spectrum of activity or a more immediate effect on very heterogeneous populations is provided. Examples of the insecticides include organic phosphorus compounds (e.g. fenitrothion (O,O-dimethyl-O-(3-methyl-4-nitrophenyl)-phosphorothioate), malathion (S-[1,2-bis(ethoxycarbonyl)-ethyl] O,O-dimethylphosphorothioate), dimethoate (O,O-dimethyl-S-(N-methylcarbamoylmethyl)phosphorodithioate), salithion (2-methoxy-4H-1,3,2-benzdioxaphosphorin-2-sulfide), diazinon (O,O-diethyl-O-(2-isopropyl-6-methyl-4-pyrimydinyl)phosphorothioate), dipterex (2,2,2-trichloro-1-hydroxyethyl-O,O-dimethylphosphonate), dichlorvos (O-(2,2-dichlorovinyl)-O,O-dimethylphosphate), etc.), carbamate compounds (e.g. MPMC (3,4-dimethylphenyl N-methylcarbamate), MTMC (m-tolyl N-methylcarbamate), BPMC (2-sec-butylphenyl N-methylcarbamate), carbaryl (1-naphthyl N-methylcarbamate), etc.) and pyrethroid compounds (e.g. permethrin (3-phenoxybenzyl-d,l-cis,trans-3-(2,2-dichlorovinyl)-2,2-dimethylcyclopropanecarboxylate), fenvalerate (α-cyano-m-phenoxybenzyl α-isopropyl-p-chlorophenylacetate, etc.).

The oxime ethers (I) of the invention formulated into an appropriate composition may be applied in a sutiable application method such as spraying, smoking, soil treatment, soil surface treatment or in combination with animal feed.

Some practical embodiments of the composition for the control of insects according to the invention are illustratively shown in the following Formulation Examples wherein % and part(s) are by weight.

FORMULATION EXAMPLE 1

Each of Compound Nos. 1 to 122 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate containing the active ingredient in a concentration of 20%.

FORMULATION EXAMPLE 2

Each of Compound Nos. 1 to 122 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder containing the active ingredient in a concentration of 20%.

FORMULATION EXAMPLE 3

Each of Compound Nos. 1, 2, 29 or 90 (3 parts) is dissolved in acetone (20 parts), talc (300 mesh) (97 parts) is added thereto, and the resultant mixture is mixed well in a pulverizer. Then, acetone is eliminated by evaporation to give a dust containing the active ingredient in a concentration of 3%.

FORMULATION EXAMPLE 4

Each of Compound Nos. 2 or 29 (5 parts), a dispersant (calcium ligninsulfonate) (2 parts) and kaolin (93 parts) are mixed well in a pulverizer. To the resultant mixture, water is added in an amount of 10%, and the resulting mixture is kneaded well and granulated by the aid of a granulator, followed by drying to give granules containing the active ingredient in a concentration of 5%.

FORMULATION EXAMPLE 5

Compound No. 2 (2 parts), a dispersant (calcium lingninsulfonate) (2 parts) and kaolin (96 parts) are mixed well in a pulverizer. Water is added to the resultant mixture in an amount of 10%. The resulting mixture is mixed well and granulated by the aid of a granulator. The granules are dried to give fine granules containing the active ingredient in a concentration of 2%.

FORMULATION EXAMPLE 6

Each of Compound Nos. 2 or 29 (5 parts), xylene (7 parts) and deodered kerosene (8 parts) are mixed well and charged into an aerozol bomb and, after setting up a valve thereon, a propellant (liquid petroleum gas) (80 parts) is charged through the valve under pressure to give an aerosole.

The following Examples show some typical test data indicating the excellent insect control activity of the oxime ethers (I). The compounds used for comparison are as follows:

| Compound No. | Chemical structure | Remarks |
| --- | --- | --- |
| A | 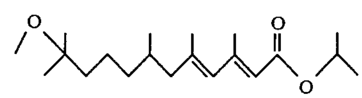 | Commercially available insecticide "methoprene" |
| B | 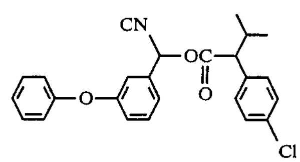 | Commericially available insecticide "fenvalerate" |
| C | 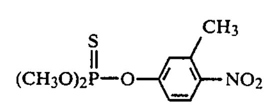 | Commercially available insecticide "fenitrothion" |

TEST EXAMPLE 1

Pupae of wax moth (*Galleria mellonella*) were collected within 20 hours from the pupation. According to the Schneiderman's method (J. Insect Physiol., 11, 1641 (1965)), a puncture of about 1 mm$^2$ was made in the right side of the thoracic dorsum of each pupa, and the wound was sealed with a designed amount of the test compound dissolved in a mixture of paraffin wax and peanut oil. The medicated pupae were kept at 28° C. in a pyrostat. The pupal cuticle at the medicated part was peeled off before emergence, and observation was made to examine the formation of the pupal cuticle, from which the average rate of reaction to the test compound was determined, and the dose of the test compound for 50% inhibition of the metamorphosis (ID$_{50}$) was calculated. The results are shown in Table 2.

TABLE 2

| Test compound No. | ID$_{50}$ (μg/pupa) |
|---|---|
| 1 | <0.001 |
| 2 | <0.001 |
| 11 | <0.001 |
| 29 | <0.001 |
| 90 | <0.001 |
| A | 2.2 |

TEST EXAMPLE 2

An emulsifiable concentrate prepared according to Formulation Example 1 was diluted with water to make a 400 fold dilution. The dilution (0.7 ml) was added to 100 ml of distilled water. Last instar larvae of common mosquito (*Culex pipiens pallens*) were released therein and reared for 7 days until their emergence. The rate of emergence was observed (two replications). The results are shown in Table 3.

TABLE 3

| Test compound No. | Concentration (ppm) | Rate of emergence (%) |
|---|---|---|
| 1 | 3.5 | 0 |
| 2 | 3.5 | 0 |
| 3 | 3.5 | 0 |
| 4 | 3.5 | 0 |
| 5 | 3.5 | 0 |
| 6 | 3.5 | 0 |
| 7 | 3.5 | 0 |
| 8 | 3.5 | 0 |
| 9 | 3.5 | 0 |
| 10 | 3.5 | 0 |
| 11 | 3.5 | 0 |
| 12 | 3.5 | 0 |
| 13 | 3.5 | 0 |
| 14 | 3.5 | 0 |
| 15 | 3.5 | 0 |
| 16 | 3.5 | 0 |
| 17 | 3.5 | 0 |
| 18 | 3.5 | 0 |
| 19 | 3.5 | 0 |
| 20 | 3.5 | 0 |
| 21 | 3.5 | 0 |
| 22 | 3.5 | 0 |
| 23 | 3.5 | 0 |
| 24 | 3.5 | 0 |
| 25 | 3.5 | 0 |
| 26 | 3.5 | 0 |
| 27 | 3.5 | 0 |
| 28 | 3.5 | 0 |
| 29 | 3.5 | 0 |
| 30 | 3.5 | 0 |
| 31 | 3.5 | 0 |
| 32 | 3.5 | 0 |
| 33 | 3.5 | 0 |
| 34 | 3.5 | 0 |
| 35 | 3.5 | 0 |
| 36 | 3.5 | 0 |
| 37 | 3.5 | 0 |
| 38 | 3.5 | 0 |
| 39 | 3.5 | 0 |
| 40 | 3.5 | 0 |
| 41 | 3.5 | 0 |
| 42 | 3.5 | 0 |
| 43 | 3.5 | 0 |
| 44 | 3.5 | 0 |
| 45 | 3.5 | 0 |
| 46 | 3.5 | 0 |
| 47 | 3.5 | 0 |
| 48 | 3.5 | 0 |
| 49 | 3.5 | 0 |
| 50 | 3.5 | 0 |
| 51 | 3.5 | 0 |
| 52 | 3.5 | 0 |
| 53 | 3.5 | 0 |
| 54 | 3.5 | 0 |
| 55 | 3.5 | 0 |
| 56 | 3.5 | 0 |
| 57 | 3.5 | 0 |
| 58 | 3.5 | 0 |
| 59 | 3.5 | 0 |
| 60 | 3.5 | 0 |
| 61 | 3.5 | 0 |
| 62 | 3.5 | 0 |
| 63 | 3.5 | 0 |
| 64 | 3.5 | 0 |
| 65 | 3.5 | 0 |
| 66 | 3.5 | 0 |
| 67 | 3.5 | 0 |
| 68 | 3.5 | 0 |
| 69 | 3.5 | 0 |
| 70 | 3.5 | 0 |
| 71 | 3.5 | 0 |
| 72 | 3.5 | 0 |
| 73 | 3.5 | 0 |
| 74 | 3.5 | 0 |
| 75 | 3.5 | 0 |
| 76 | 3.5 | 0 |
| 77 | 3.5 | 0 |
| 78 | 3.5 | 0 |
| 79 | 3.5 | 0 |
| 80 | 3.5 | 0 |
| 81 | 3.5 | 0 |
| 82 | 3.5 | 0 |
| 83 | 3.5 | 0 |
| 84 | 3.5 | 0 |
| 85 | 3.5 | 0 |
| 86 | 3.5 | 0 |
| 87 | 3.5 | 0 |
| 88 | 3.5 | 0 |
| 89 | 3.5 | 0 |
| 90 | 3.5 | 0 |
| 91 | 3.5 | 0 |
| 92 | 3.5 | 0 |
| 93 | 3.5 | 0 |
| 94 | 3.5 | 0 |
| 95 | 3.5 | 0 |
| 96 | 3.5 | 0 |
| 97 | 3.5 | 0 |
| 98 | 3.5 | 0 |
| 99 | 3.5 | 0 |
| 100 | 3.5 | 0 |
| 101 | 3.5 | 0 |
| 102 | 3.5 | 0 |
| 103 | 3.5 | 0 |
| 104 | 3.5 | 0 |
| 105 | 3.5 | 0 |
| 106 | 3.5 | 0 |
| 107 | 3.5 | 0 |
| 108 | 3.5 | 0 |
| 109 | 3.5 | 0 |
| 110 | 3.5 | 0 |
| 111 | 3.5 | 0 |
| 112 | 3.5 | 0 |
| 113 | 3.5 | 0 |
| 114 | 3.5 | 0 |
| 115 | 3.5 | 0 |
| 116 | 3.5 | 0 |
| 117 | 3.5 | 0 |
| 118 | 3.5 | 0 |
| 119 | 3.5 | 0 |
| 120 | 3.5 | 0 |
| 121 | 3.5 | 0 |
| 122 | 3.5 | 0 |
| A | 3.5 | 0 |
| Untreated | — | 90 |

TEST EXAMPLE 3

An emulsifiable concentrate prepared according to Formulation Example 1 was diluted with water to a designed dilution. The dilution (0.5 ml) was added to 100 ml of distilled water. Twenty last instar larvae of common mosquito (*Culex pipiens pallens*) were released therein and reared for 7 days until their emergence. The 50% emergence inhibition concentration ($IC_{50}$) was determined (two replications). The results are shown in Table 4 wherein $PI_{50}$ corresponds to $-\log IC_{50}$.

TABLE 4

| Test Compound No. | $PI_{50}$ |
|---|---|
| 1 | 4.0 |
| 2 | 7.4 |
| 4 | 5.5 |
| 5 | 4.4 |
| 7 | 4.4 |
| 11 | 6.6 |
| 12 | 4.1 |
| 14 | 4.0 |
| 20 | 5.1 |
| 21 | 4.7 |
| 23 | 4.5 |
| 24 | 6.6 |
| 25 | 4.5 |
| 26 | 5.0 |
| 29 | 6.5 |
| 36 | 4.0 |
| 39 | 4.0 |
| 41 | 4.1 |
| 42 | 4.0 |
| 51 | 4.6 |
| 55 | 4.4 |
| 56 | 3.9 |
| 57 | 4.8 |
| 60 | 4.3 |
| 64 | 3.9 |
| 65 | 4.7 |
| 66 | 3.9 |
| 68 | 4.3 |
| 69 | 4.5 |
| 78 | 4.0 |
| 87 | 4.0 |
| 90 | 7.6 |
| 97 | 4.3 |
| 101 | 5.8 |
| 102 | 6.2 |
| 106 | 4.2 |
| 115 | 4.4 |
| 116 | 4.9 |
| A | 3.7 |

TEST EXAMPLE 4

In the same manner as in Test Example 2 but rearing yellow fever mosquito (*Aedes aegypti*) instead of common mosquito (*Culex pipiens pallens*), the rate of emergence was observed (two replications). The results are shown in Table 5.

TABLE 5

| Test compound No. | Concentration (ppm) | Rate of emergence (%) |
|---|---|---|
| 1 | 3.5 | 0 |
| 2 | 3.5 | 0 |
| 3 | 3.5 | 0 |
| 4 | 3.5 | 0 |
| 5 | 3.5 | 0 |
| 11 | 3.5 | 0 |
| 12 | 3.5 | 0 |
| 14 | 3.5 | 0 |
| 16 | 3.5 | 0 |
| 20 | 3.5 | 0 |
| 21 | 3.5 | 0 |
| 23 | 3.5 | 0 |
| 24 | 3.5 | 0 |
| 25 | 3.5 | 0 |
| 26 | 3.5 | 0 |
| 29 | 3.5 | 0 |
| 38 | 3.5 | 0 |
| 39 | 3.5 | 0 |
| 48 | 3.5 | 0 |
| 51 | 3.5 | 0 |
| 54 | 3.5 | 0 |
| 55 | 3.5 | 0 |
| 57 | 3.5 | 0 |
| 87 | 3.5 | 0 |
| 90 | 3.5 | 0 |
| 92 | 3.5 | 0 |
| 101 | 3.5 | 0 |
| 102 | 3.5 | 0 |
| 112 | 3.5 | 0 |
| 116 | 3.5 | 0 |
| Untreated | — | 87.5 |

TEST EXAMPLE 5

In the same manner as in Test Example 3 but rearing yellow fever mosquito (*Aedes aegypti*) instead of common mosquito (*Culex pipiens pallens*), the 50% emergence inhibition concentration ($IC_{50}$) was examined (two replications). The results are shown in Table 6 wherein $PI_{50}$ corresponds to $-\log IC_{50}$.

TABLE 6

| Test Compound No. | $PI_{50}$ |
|---|---|
| 2 | 7.2 |
| 101 | 7.4 |
| 102 | 7.6 |
| A | 2.7 |

TEST EXAMPLE 6

Powdered animal feed (2 g) was thoroughly mixed with bran (14 g). An emulsifiable concentrate prepared according to Formulation Example 1 was diluted with water to a designed concentration and added to the above mixture. The resultant mixture was stirred well to make an artificial culture. Thirty larvae of housefly (*Musca domestica*) were reared therein until their pupation. The obtained pupae were placed into a plastic cup, and the rate of emergence was determined. According to the following equation, the emergence inhibition (%) was calculated:

Emergence inhibition (%) =

$$\left(1 - \frac{\text{Rate of emergence in treated plot}}{\text{Rate of emergence in untreated plot}}\right) \times 100$$

The results are shown in Table 7.

TABLE 7

| Test compound No. | Emergence inhibition (%) | | |
|---|---|---|---|
| | 3 ppm | 1 ppm | 0.3 ppm |
| 1 | 100 | 100 | 100 |
| 2 | 100 | 100 | 100 |
| 4 | 100 | 97 | 80 |
| 5 | 100 | 100 | 92 |
| 25 | 97 | 33 | 8 |
| 28 | 100 | 100 | 100 |
| 29 | 100 | 100 | 100 |
| 33 | 100 | 96 | 79 |
| 36 | 79 | 33 | 24 |
| 39 | 97 | 52 | 3 |
| 41 | 100 | 90 | 51 |
| 42 | 96 | 96 | 23 |
| 48 | 100 | 100 | 100 |
| 49 | 92 | 68 | 14 |
| 51 | 96 | 92 | 46 |

TABLE 7-continued

| Test compound No. | Emergence inhibition (%) | | |
|---|---|---|---|
| | 3 ppm | 1 ppm | 0.3 ppm |
| 54 | 100 | 100 | 100 |
| 57 | 100 | 96 | 73 |
| 60 | 87 | 40 | 5 |
| 63 | 97 | 62 | 0 |
| 64 | 84 | 42 | 0 |
| 65 | 100 | 85 | 32 |
| 66 | 100 | 40 | 42 |
| 68 | 88 | 22 | 22 |
| 69 | 97 | 38 | 14 |
| 70 | 93 | 25 | 0 |
| 72 | 73 | 22 | 4 |
| 87 | 100 | 38 | 0 |
| 88 | 100 | 100 | 96 |
| 89 | 100 | 97 | 26 |
| 90 | 100 | 100 | 100 |
| 95 | 100 | 97 | 78 |
| 103 | 100 | 100 | 100 |
| 105 | 100 | 93 | 54 |
| 106 | 100 | 100 | 52 |
| 115 | 100 | 100 | 100 |
| 116 | 100 | 100 | 100 |
| 120 | 92 | 74 | 0 |
| A | 60 | 13 | 2 |

TEST EXAMPLE 7

An emulsifiable concentrate prepared according to Formulation Example 1 was diluted with water to a designed concentration. The resultant dilution (50 ml) was added to feed for domestic fowl (100 g) and thoroughly mixed. The thus obtained mixture was fed to groups of fowls (each group consisting of three animals) at a daily dose of 100 g/fowl for 2 days, whereupon their droppings were collected. Two hundreds eggs of housefly (Musca domestica) were incubated in the droppings until their pupation. The obtained pupae were placed into another container, and the 50% emergence inhibition concentration ($IC_{50}$) was examined. The results are shown in Table 8.

TABLE 8

| Test Compound No. | $IC_{50}$ (ppm) |
|---|---|
| 1 | 1.9 |
| 2 | 2.6 |
| 29 | 1.2 |
| 90 | 2.2 |
| A | 32 |

TEST EXAMPLE 8

Each fifty imagoes of male and female houseflies (Musca domestica) were put in a cage. Separately, powdered feed (2 g), bran (14 g) and water (28 ml) were thoroughly mixed to make an artificial culture and one hundred 4-day-old larvae of housefly were reared therein. An emulsifiable concentrate of Compound No. 29 prepared according to Formulation Example 1 as well as its mixture with Compound B (fenvalerate) and Compound C (fenitrothion) was sprayed to the cage and the culture at a spray volume of 20 ml. After the spraying, the culture was put in the cage, and the numbers of the imagoes within the cage were observed with lapse of days and evaluated in terms of "corrected density index", which was calculated according to the following equation:

$$\text{Corrected density index} = \frac{\text{Number of imago before treatment in untreated plot} \times \text{Number of imago after treatment in treated plot}}{\text{Number of imago after treatment in untreated plot} \times \text{Number of imago before treatment in treated plot}} \times 100$$

The results are shown in Table 9.

TABLE 9

| Compound No. | Concentration (ppm) | Corrected density index | | | | |
|---|---|---|---|---|---|---|
| | | 1 day | 2 days | 5 days | 16 days | 22 days |
| 29 | 5 | 98 | 98 | 100 | 14 | 13 |
| B | 10 | 67 | 73 | 74 | 46 | 48 |
| C | 10 | 31 | 24 | 22 | 71 | 78 |
| 29/B | 5/10 | 71 | 69 | 67 | 6 | 2 |
| 29/C | 5/10 | 47 | 36 | 36 | 6 | 7 |

What is claimed is:

1. A compound of the formula:

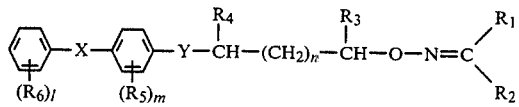

wherein $R_1$ and $R_2$ are, same or different, each a hydrogen atom, a $C_1$-$C_3$ alkyl group optionally substituted with halogen, an alkoxyalkyl or alkylthioalkyl group of the formula: $R_7$—Z—$(CH_2)_q$—, a $C_2$-$C_3$ alkenyl group, a $C_2$-$C_4$ alkynyl group, a $C_1$-$C_2$ alkoxy group, a $C_1$-$C_2$ alkylthio group, a phenyl group, a pyridyl group, a furyl group or a thienyl group, or $R_1$ and $R_2$ may be combined together to form a saturated or unsaturated 5- or 6-membered ring optionally having not more than 2 oxygen or sulfur atoms within the ring, $R_3$ and $R_4$ are, same or different, each a hydrogen atom or a methyl group, $R_5$ is a methyl group or a halogen atom, $R_6$ is a $C_1$-$C_4$ alkyl group, a methoxy group, a halogen atom, a trifluoromethyl group or a nitro group, $R_7$ is a methyl group or an ethyl group, X is an oxygen atom, a sulfur atom or a methylene group, Y and Z are each an oxygen atom or a sulfur atom, l is an integer of 0 to 5, m is an integer of 0 to 4, n is an integer of 0 to 2 and q is an integer of 1 or 2.

2. The compound according to claim 1, wherein $R_1$ is a hydrogen atom or a methyl group, $R_2$ is a methyl group, an ethyl group or a vinyl group, $R_3$ and $R_4$ are, same or different, each a hydrogen atom or a methyl group, $R_6$ is a methyl group, a fluorine atom or a chlorine atom, X is an oxygen atom or a methylene group, Y is an oxygen atom, l is 0 or 1, m is 0 and n is 0.

3. The compound according to claim 1, wherein $R_1$, $R_3$ and $R_4$ are each a hydrogen atom, $R_2$ is a methyl group, X and Y are each an oxygen atom, l is 0, m is 0 and n is 0.

4. The compound according to claim 1, wherein $R_1$, $R_3$ and $R_4$ are each a hydrogen atom, $R_2$ is an ethyl group, X and Y are each an oxygen atom, l is 0, m is 0 and n is 0.

5. The compound according to claim 1, wherein $R_1$, $R_3$ and $R_4$ are each a hydrogen atom, $R_2$ is a methyl group, $R_6$ is a fluorine atom at the 3-position, X and Y are each an oxygen atom, m is 0 and n is 0.

6. The compound according to claim 1, wherein $R_1$, $R_3$ and $R_4$ are each a hydrogen atom, $R_2$ is an ethyl group, $R_6$ is a fluorine atom at the 3-position, X and Y are each an oxygen atom, m is 0 and n is 0.

7. The compound according to claim 1, wherein $R_1$, $R_3$ and $R_4$ are each a hydrogen atom, $R_2$ is an ethyl group, X is a methylene group, Y is an oxygen atom, l is 0, m is 0 and n is 0.

8. The compound according to claim 1, wherein $R_1$, $R_3$ and $R_4$ are each a hydrogen atom, $R_2$ is an ethyl group, X and Y are each an oxygen atom, $R_6$ is fluorine atoms at the 3 and 5-positions, m is 0 and n is 0.

9. The compound according to claim 1, wherein $R_1$ and $R_3$ are each a hydrogen atom, $R_2$ and $R_4$ are each a methyl group, $R_6$ is a fluorine atom at the 3-position, X and Y are each an oxygen atom, m is 0 and n is 0.

10. The compound according to claim 1, wherein $R_1$ and $R_3$ are each a hydrogen atom, $R_2$ is an ethyl group, $R_4$ is a methyl group, $R_6$ is a fluorine atom at the 3-position, X and Y are each an oxygen atom, m is 0 and n is 0.

11. The compound according to claim 1, wherein X and Y are each an oxygen atom, $R_1$ is a hydrogen atom, $R_2$ is an ethyl group, $R_3$ is a hydrogen atom, $R_4$ is a methyl group, $R_5$ and $R_6$ are each a hydrogen atom and n is 0.

12. A composition for controlling insects which comprises as an active ingredient an insecticidally effective amount of the compound according to claim 1 and an inert carrier or diluent.

13. A composition for controlling insects which comprises as an active ingredient an insecticidally effective amount of the compound according to claim 2 and an inert carrier or diluent.

14. A composition for controlling insects which comprises as an active ingredient an insecticidally effective amount of the compound according to claim 3 and an inert carrier or diluent.

15. A composition for controlling insects which comprises as an active ingredient an insecticidally effective amount of the compound according to claim 11 and an inert carrier or diluent.

16. A method for controlling insects selected from the group consisting of Hemiptera, Lepidoptera, Coleoptera, Diptera, Dictyoptera, Orthoptera, Hemoptera, Hymenoptera and Aphaniptera comprising applying an insecticidally effective amount of a compound according to claim 1 to said insects.

17. A method for controlling insects selected from the group consisting of Hemiptera, Lepidoptera, Coleoptera, Diptera, Dictyoptera, Orthoptera, Hemoptera, Hymenoptera and Aphaniptera comprising applying an insecticidally effective amount of a compound according to claim 2 to said insects.

18. A method for controlling insects selected from the group consisting of Hemiptera, Lepidoptera, Coleoptera, Diptera, Dictyoptera, Orthoptera, Hemoptera, Hymenoptera and Aphaniptera comprising applying an insecticidally effective amount of a compound according to claim 3 to said insects.

19. A method for controlling insects selected from the group consisting of Hemiptera, Lepidoptera, Coleoptera, Diptera, Dictyoptera, Orthoptera, Hemoptera, Hymenoptera and Aphaniptera comprising applying an insecticidally effective amount of a compound according to claim 11 to said insects.

20. A method for controlling insects selected from the group consisting of Hemiptera, Lepidoptera, Coleoptera, Diptera, Dictyoptera, Orthoptera, Hemoptera, Hymenoptera and Aphaniptera in animal excrement comprising applying an effective amount of a compound according to claim 1 to animal feed to be consumed by an animal, whereby the animal excrement will contain an insecticidally effective amount of said compound according to claim 1.

21. A method for controlling insects selected from the group consisting of Hemiptera, Lepidoptera, Coleoptera, Diptera, Dictyoptera, Orthoptera, Hemoptera, Hymenoptera and Aphaniptera in animal excrement comprising applying an effective amount of a compound according to claim 2 to animal feed to be consumed by an animal, whereby the animal excrement will contain an insecticidally effective amount of said compound according to claim 2.

22. A method for controlling insects selected from the group consisting of Hemiptera, Lepidoptera, Coleoptera, Diptera, Dictyoptera, Orthoptera, Hemoptera, Hymenoptera and Aphaniptera in animal excrement comprising applying an effective amount of a compound according to claim 3 to animal feed to be consumed by an animal, whereby the animal excrement will contain an insecticidally effective amount of said compound according to claim 3.

23. A method for controlling insects selected from the group consisting of Hemiptera, Lepidoptera, Coleoptera, Diptera, Dicyoptera, Orthoptera, Hemoptera, Hymenoptera and Aphaniptera in animal excrement comprising applying an effective amount of a compound according to claim 17 to animal feed to be consumed by an animal, whereby the animal excrement will contain an insecticidally effective amount of said compound according to claim 11.

24. An animal feed composition comprising an animal feed and an insecticidally effective amount of a compound according to claim 1, said insecticidally effective amount being an amount effective for controlling insects in said animal feed or for controlling insects in animal excrement from animals having consumed said animal feed.

* * * * *